(12) United States Patent
Lacoste et al.

(10) Patent No.: US 8,206,978 B2
(45) Date of Patent: Jun. 26, 2012

(54) GREEN FLUORESCENT PROTEIN OPTIMIZED FOR EXPRESSION WITH SELF-CLEAVING POLYPEPTIDES

(75) Inventors: Arnaud Lacoste, Cambridge, MA (US); Neptune Mizrahi, Los Angeles, CA (US)

(73) Assignee: Inseron, Inc., Los Angeles, CA (US)

( * ) Notice: Subject to any disclaimer, the term of this patent is extended or adjusted under 35 U.S.C. 154(b) by 260 days.

(21) Appl. No.: 12/521,798

(22) PCT Filed: Dec. 28, 2007

(86) PCT No.: PCT/US2007/026389
§ 371 (c)(1),
(2), (4) Date: Dec. 8, 2009

(87) PCT Pub. No.: WO2008/085502
PCT Pub. Date: Jul. 17, 2008

(65) Prior Publication Data
US 2011/0099646 A1   Apr. 28, 2011

Related U.S. Application Data

(60) Provisional application No. 60/879,112, filed on Jan. 5, 2007.

(51) Int. Cl.
*C07K 1/00* (2006.01)
*C12N 15/00* (2006.01)
*C07H 21/02* (2006.01)

(52) U.S. Cl. .................. 435/320.1; 435/235.1; 530/350; 536/23.1

(58) Field of Classification Search .................. None
See application file for complete search history.

(56) References Cited

U.S. PATENT DOCUMENTS

| | | | |
|---|---|---|---|
| 5,491,084 | A | 2/1996 | Chalfie et al. |
| 7,410,765 | B2 | 8/2008 | Lacoste et al. |
| 2002/0197676 | A1 | 12/2002 | Lukyanov et al. |
| 2003/0013849 | A1 | 1/2003 | Ward et al. |
| 2003/0106078 | A1 | 6/2003 | Falkowski et al. |
| 2005/0142637 | A1 | 6/2005 | Haddock et al. |
| 2005/0196768 | A1 | 9/2005 | Campbell et al. |

FOREIGN PATENT DOCUMENTS

WO   WO 96/23810 A1   8/1996

OTHER PUBLICATIONS

Ando et al., "An Optical Marker Based on the UV-induced Green-to-red Photoconversion of a Fluorescent Protein" *PNAS*, Oct. 1, 2002; 99(20):12651-12656.
Bulina et al., "Interconversion of *Anthozoa* GRP-like Fluorescent and Non-fluorescent Proteins by Mutagenesis" *BMC Biochemistry*, 2002; 3:7. 8 pages.
Campbell et al., "A Monomeric Red Fluorescent Protein" *PNAS*, Jun. 11, 2002; 99(12):7877-7882.
Cubitt et al., "Understanding, Improving and Using Green Fluorescent Proteins" *TIBS*, Nov. 1, 1995; 20(11):448-455.
Erickson et al., "DsRed as a Potential FRET Partner with CFP and GFP" *Biophysical Journal*, Jul. 2003; 85:599-611.
European Search Report for European Patent Application No. 07868067.5, Dec. 20, 2010; 7 pgs.
Fradkov et al., "Novel Fluorescent Protein from Discosoma Coral and its Mutants Possesses a Unique Far-red Fluorescence" *FEBS Lett.*, Aug. 18, 2000; 479(3):127-130.
"Green Fluorescent Protein" [online]. Proteopedia, last modified Nov. 14, 2011 [retrieved on Dec. 12, 2011]. Retrieved from the Internet: <URL:http://proteopedia.org/wiki/index.php/GFP>; 12 pgs.
Gurskaya et al., "Color Transitions in Coral's Fluorescent Proteins by Site-directed Mutagenesis" *BMC Biochemistry*, 2001; 2:6. 7 pages.
Heim et al., "Wavelength Mutations and Posttranslational Autoxidation of Green Fluorescent Protein" *Proc. Natl. Acad. Sci. USA*, Dec. 1994; 91:12501-12504.
Heim et al., "Engineering Green Fluorescent Protein for Improved Brightness, Longer Wavelengths and Fluorescence Resonance Energy Transfer" *Current Biology*, 1996; 6:178-182.
International Search Report and Written Opinion for PCT application PCT/US07/26389, Sep. 26, 2008; 8 pgs.
International Preliminary Report on Patentability, for PCT application PCT/US07/26389, Jul. 7, 2009; 5 pgs.
Lippincott-Schwartz et al., "Development and Use of Fluorescent Protein Markers in Living Cells" *Science*, Apr. 4, 2003; 300:87-91.
Martynov et al., "Alternative Cyclization in GFP-like Proteins Family" *J. Biol. Chem.*, Jun. 15, 2001; 276(24):21012-21016.
Matz et al., "Fluorescent Proteins from Nonbioluminescent Anthozoa Species" *Nat. Biotechnol.*, Oct. 1999; 17(10):969-973.
National Center for Biotechnology Information, National Library of Medicine, National Institutes of Health, GenBank Locus AAZ14789, Accession No. AAZ14789, "GFP-type orange fluorescent protein [Corynactis californica]" [online]. Bethesda, MD [retrieved on May 1, 2012]. Retrieved from the Internet<URL:http://www.ncbi.nlm.nih.gov/protein/AAZ14789>; 1 pg.
Prasher et al., "Primary Structure of the Aequorea Victoria Green-Fluorescent Protein" *Gene.*, Feb. 15, 1992; 111(2):229-233.
Schnitzler, "Spectral Diversity of Fluorescent Proteins from the Anthozoan Corynactis Californica" *Mar. Biotechnol. (NY)*, May-Jun. 2008; 10(3):328-342. Epub Mar. 11, 2008.
Shagin et al., "GFP-like Proteins as Ubiquitous Metazoan Superfamily: Evolution of Functional Features and Structural Complexity" *Mol. Biol. Evol.*, 2004; 21(5):841-850.
Shaner et al., "Improved Monomeric Red, Orange and Yellow Fluorescent Proteins Defived from *Discosoma* Sp. Red Fluorescent Protein" *Nat. Biotechnol.*, Dec. 2004; 22(12):1567-1572. Epub Nov. 21, 2004.
Shaner et al., "A Guide to Choosing Fluorescent Proteins" *Nat. Methods*, Dec. 2005; 2(12):905-909.

(Continued)

*Primary Examiner* — Patricia A Duffy
(74) *Attorney, Agent, or Firm* — Mueting, Raasch & Gebhardt, P.A.

(57) ABSTRACT

The present invention provides a new fluorescent protein, engineered to facilitate release from self-cleaving peptides.

20 Claims, 4 Drawing Sheets

OTHER PUBLICATIONS

Szymczak et al., "Correction of Multi-Gene Deficiency in vivo Using a single 'self-cleaving' 2A peptide-based retroviral vector" *Nat. Biotechnol.*, May 2004; 22(5):589-594. With Addendum, Nat. Biotechnol., Jun. 2004; 22(6):760.

Tatusova et al., "BLAST 2 Sequences, a New Tool for Compairing Protein and Nucleotide Sequences" *FEMS Microbiology Letters*, 1999; 174:247-250.

Yanushevich et al., "A Strategy for the Generation of Non-Aggregating Mutants of Anthozoa Fluorescent Proteins" *FEBS Lett.*, Jan. 30, 2002; 511(1-3):11-14.

ATGGTGAGCCTGAGCAAGGGCCACGTGATCGCCCAGGACGTGACCATGATCTACCGCATGGACGGCTGCGT
GAACGGCCACAACTTCACCATCGAGGGCGAGGGTAACGGCAAGCCCTACGAGGGCCAGCAAACCCTGAAGC
TCCGCATCACCAAGGGCGGCCCCCTGCCCTTCGCCTTCGACATCTTGAGCGCCACCTTCACCTACGGCAAC
CGCTGCTTCACCTTCTACCCCGAGGACATCGCCGACTACTTCAAGCAGAGCTTCCCCGAGGGCCACAGCTG
GGAACGCACCATGATGTACGAGGACGGCGCCTGCTCCACCGCCAGCGCCCACATCAGCCTGAAGGGCACCT
CCTTCGTCCATAATAGCACTTTCCACGGCGTCAACTTCCCCGCCAATGGCCCCGTCATGCAGAAAAAGACT
CTCAATTGGGAACCCAGCTCCGAGAAGATCACCGCCTGCGAGGGCGCCCTGAAGGGGGACGTGACCATGTT
CCTCCTCCTGGAGGGCGGCCTGAAGCACAAGTGCCAGTTCCAGACCACCTACGAGGCCCACAAGGCCGTGA
AGATGCCCCCCTCCCACATCATCGAGCACCGCCTGGTGCGCAGCGAGGTGGGCGCAGCCGTGCAGCTGCGC
GAGCACGCCGTGGCCCGCCACTTCATCGCC

*Fig. 1A*

MVSLSKGHVIAQDVTMIYRMDGCVNGHNFTIEGEGNGKPYEGQQTLKLRITKGGPLPFAFDILSATFTYGN
RCFTFYPEDIADYFKQSFPEGHSWERTMMYEDGACSTASAHISLKGTSFVHNSTFHGVNFPANGPVMQKKT
LNWEPSSEKITACEGALKGDVTMFLLLEGGLKHKCQFQTTYEAHKAVKMPPSHIIEHRLVRSEVGAAVQLR
EHAVARHFIA

*Fig. 1B*

```
            1                                                             60
native     MSLSK-HVI AQDVTMIYRM DGCVNGHSFT IEGEGTGKPY EGQQTLKLRI TKGGPLPFAF
seqID2     MVSLSKGHVI AQDVTMIYRM DGCVNGHNFT IEGEGNGKPY EGQQTLKLRI TKGGPLPFAF
Consensus   mSLSK.HVI AQDVTMIYRM DGCVNGHnFT IEGEGnGKPY EGQQTLKLRI TKGGPLPFAF 61                                                           120
native     DILSATFTYG NRCFTFYPED IADYFKQSFP EGHSWERTMM YEDGACSTAS AHISLKGTSF
seqID2     DILSATFTYG NRCFTFYPED IADYFKQSFP EGHSWERTMM YEDGACSTAS AHISLKGTSF
Consensus  DILSATFTYG NRCFTFYPED IADYFKQSFP EGHSWERTMM YEDGACSTAS AHISLKGTSF 121                                                          180
native     VHNSTFHGVN FPANGPVMQK KTLNWEPSSE KITACEGALK GDVTMFLLLE GGLKHKCQFQ
seqID2     VHNSTFHGVN FPANGPVMQK KTLNWEPSSE KITACEGALK GDVTMFLLLE GGLKHKCQFQ
Consensus  VHNSTFHGVN FPANGPVMQK KTLNWEPSSE KITACEGALK GDVTMFLLLE GGLKHKCQFQ 181                          223
native     TTYEAHKAVK MPPSHIIEHR LVRSEVGAAV QLREHAVAKH FIA
seqID2     TTYEAHKAVK MPPSHIIEHR LVRSEVGAAV QLREHAVARH FIA
Consensus  TTYEAHKAVK MPPSHIIEHR LVRSEVGAAV QLREHAVArH FIA
```

*Fig. 4*

SEQUENCE LISTING

```
<160> NUMBER OF SEQ ID NOS: 6

<210> SEQ ID NO 1
<211> LENGTH: 671
<212> TYPE: DNA
<213> ORGANISM: Artificial
<220> FEATURE:
<223> OTHER INFORMATION: Nucleotide Sequence of Engineered Corynactis
      viridis fluorescent protein, with termination codon

<400> SEQUENCE: 1
atggtgagcc tgagcaaggg ccacgtgatc gcccaggacg tgaccatgat caccgcatgg      60
acggctgcgt gaacggccac aacttcacca tcgagggcga gggtaacggc aagccctacg     120
agggccagca aaccctgaag ctccgcatca ccaaggcgg cccctgccc ttcgccttcg      180 acatcttgag cgccaccttc acctacggca accgctgctt caccttctac cccgaggaca     240
```

-continued

```
tcgccgacta cttcaagcag agcttccccg agggccacag ctgggaacgc accatgatgt    300
acgaggacgg cgcctgctcc accgccagcg cccacatcag cctgaagggc acctccttcg    360
tccataatag cactttccac ggcgtcaact tccccgccaa tggccccgtc atgcagaaaa    420
agactctcaa ttgggaaccc agctccgaga agatcaccgc ctgcgagggc gccctgaagg    480
gggacgtgac catgttcctc ctcctggagg gcggcctgaa gcacaagtgc cagttccaga    540
ccacctacga ggcccacaag gccgtgaaga tgcccccctc ccacatcatc gagcaccgcc    600
tggtgcgcag cgaggtgggc gcagccgtgc agctgcgcga gcacgccgtg gcccgccact    660
tcatcgccta a                                                         671
```

<210> SEQ ID NO 2
<211> LENGTH: 668
<212> TYPE: DNA
<213> ORGANISM: Artificial
<220> FEATURE:
<223> OTHER INFORMATION: Nucleotide Sequence of engineered Corynactis
      viridis fluorescent protein

<400> SEQUENCE: 2

```
atggtgagcc tgagcaaggg ccacgtgatc gcccaggacg tgaccatgat ctaccgcatg     60
gacggctgcg tgaacggcca caacttcacc atcgagggcg agggtaacgg caagcctacg    120
agggccagca aaccctgaag ctccgcatca ccaaggcgg cccctgccc ttcgccttcg    180 acatcttgag cgccaccttc acctacggca accgctgctt caccttctac cccgaggaca    240
tcgccgacta cttcaagcag agcttccccg agggccacag ctgggaacgc accatgatgt    300
acgaggacgg ggcctgctcc accgccaggg cccacatcag cctgaagggc acctccttcg    360
tccataatag cactttccac ggcgtcaact tccccgccaa tggccccgtc atgcagaaaa    420
agactctcaa ttgggaaccc agctccgaga agatcaccgc ctgcgagggc gccctgaagg    480
gggacgtgac catgttcctc ctcctggagg gcggcctgaa gcacaagtgc cagttccaga    540
ccacctacga ggcccacaag gccgtgaaga tgcccccctc ccacatcatc gagcaccgcc    600
tggtgcgcag cgaggtgggc gcagccgtgc agctgcgcga gcacgccgtg gcccgccact    660
tcatcgcc                                                             668
```

<210> SEQ ID NO 3
<211> LENGTH: 223
<212> TYPE: PRT
<213> ORGANISM: artificial
<220> FEATURE:
<223> OTHER INFORMATION: Amino Acid sequence of engineered Corynactis
      viridis fluorescent protein

<400> SEQUENCE: 3

```
Met Val Ser Leu Ser Lys Gly His Val Ile Ala Gln Asp Val Thr Met
1               5                   10                  15

Ile Tyr Arg Met Asp Gly Cys Val Asn Gly His Asn Phe Thr Ile Glu
            20                  25                  30

Gly Glu Gly Asn Gly Lys Pro Tyr Glu Gly Gln Gln Thr Leu Lys Leu
        35                  40                  45

Arg Ile Thr Lys Gly Gly Pro Leu Pro Phe Ala Phe Asp Ile Leu Ser
    50                  55                  60

Ala Thr Phe Thr Tyr Gly Asn Arg Cys Phe Thr Phe Tyr Pro Glu Asp
65                  70                  75                  80

Ile Ala Asp Tyr Phe Lys Gln Ser Phe Pro Glu Gly His Ser Trp Glu
                85                  90                  95
```

```
Arg Thr Met Met Tyr Glu Asp Gly Ala Cys Ser Thr Ser Ala His
            100                 105                 110
Ile Ser Leu Lys Gly Thr Ser Phe Val His Asn Ser Thr Phe His Gly
        115                 120                 125
Val Asn Phe Pro Ala Asn Gly Pro Val Met Gln Lys Lys Thr Leu Asn
    130                 135                 140
Trp Glu Pro Ser Ser Glu Lys Ile Thr Ala Cys Glu Gly Ala Leu Lys
145                 150                 155                 160
Gly Asp Val Thr Met Phe Leu Leu Glu Gly Gly Leu Lys His Lys
                165                 170                 175
Cys Gln Phe Gln Thr Thr Tyr Glu Ala His Lys Ala Val Lys Met Pro
            180                 185                 190
Pro Ser His Ile Ile Glu His Arg Leu Val Arg Ser Glu Val Gly Ala
        195                 200                 205
Ala Val Gln Leu Arg Glu His Ala Val Ala Arg His Phe Ile Ala
    210                 215                 220
```

<210> SEQ ID NO 4
<211> LENGTH: 663
<212> TYPE: DNA
<213> ORGANISM: Corynactis viridis

<400> SEQUENCE: 4

```
atgagcctga gcaagcacgt gatcgcccag gacgtgacca tgatctaccg catggacggc      60
tgcgtgaacg gccacagctt caccatcgag ggcgagggta ccggcaagcc ctacgagggc     120
cagcaaaccc tgaagctccg catcaccaag ggcggccccc tgcccttcgc cttcgacatc     180
ttgagcgcca ccttcaccta cggcaaccgc tgcttcacct tctacccccga ggacatcgcc    240
gactacttca gcagagcttt ccccgagggc cacatgggaa cgcaccatga tgtacgagga    300
cggcgcctgc tccaccccag cgcccacatc agcctgaagg caccagcttc cgtgcacaac    360
agcaccttcc acggggtgaa cttccccgcc aacggccccg tgatgcagaa gaagaccctg    420
aactgggagc ccagctccga gaagatcacc gcctgcgagg gcgccctgaa ggggacgtg     480
accatgttcc tcctcctgga gggcggcctg aagcacaagt gccagttcca gaccacctac    540
gaggcccaca aggccgtgaa gatgccccccc tcccacatca tcgagcaccg cctggtgcgc    600
agcgaggtgg gcgcggccgt gcagctgcgc gagcacgccg tggccaagca cttcatcgcc    660
taa                                                                  663
```

<210> SEQ ID NO 5
<211> LENGTH: 221
<212> TYPE: PRT
<213> ORGANISM: corynactis viridis

<400> SEQUENCE: 5

```
Met Ser Leu Ser Lys His Val Ile Ala Gln Asp Val Thr Met Ile Tyr
1               5                   10                  15
Arg Met Asp Gly Cys Val Asn Gly His Ser Phe Thr Ile Glu Gly Glu
            20                  25                  30
Gly Thr Gly Lys Pro Tyr Glu Gly Gln Gln Thr Leu Lys Leu Arg Ile
        35                  40                  45
Thr Lys Gly Gly Pro Leu Pro Phe Ala Phe Asp Ile Leu Ser Ala Thr
    50                  55                  60
Phe Thr Tyr Gly Asn Arg Cys Phe Thr Phe Tyr Pro Glu Asp Ile Ala
65                  70                  75                  80

Asp Tyr Phe Lys Gln Ser Phe Pro Glu Gly His Ser Trp Glu Arg Thr
```

```
                     85                  90                  95
Met Met Tyr Glu Asp Gly Ala Cys Ser Thr Ala Ser Ala His Ile Ser
                100                 105                 110
Leu Lys Gly Thr Ser Phe Val His Asn Ser Thr Phe His Gly Val Asn
                115                 120                 125
Phe Pro Ala Asn Gly Pro Val Met Gln Lys Lys Thr Leu Asn Trp Glu
130                 135                 140
Pro Ser Ser Glu Lys Ile Thr Ala Cys Glu Gly Ala Leu Lys Gly Asp
145                 150                 155                 160
Val Thr Met Phe Leu Leu Leu Glu Gly Gly Leu Lys His Lys Cys Gln
                165                 170                 175
Phe Gln Thr Thr Tyr Glu Ala His Lys Ala Val Lys Met Pro Pro Ser
                180                 185                 190
His Ile Ile Glu His Arg Leu Val Arg Ser Glu Val Gly Ala Ala Val
                195                 200                 205
Gln Leu Arg Glu His Ala Val Ala Lys His Phe Ile Ala
                210                 215                 220

<210> SEQ ID NO 6
<211> LENGTH: 221
<212> TYPE: PRT
<213> ORGANISM: artificial
<220> FEATURE:
<223> OTHER INFORMATION: Consensus Sequence

<400> SEQUENCE: 6

Met Ser Leu Ser Lys His Val Ile Ala Gln Asp Val Thr Met Ile Tyr
1                5                  10                  15
Arg Met Asp Gly Cys Val Asn Gly His Asn Phe Thr Ile Glu Gly Glu
                20                  25                  30
Gly Asn Gly Lys Pro Tyr Glu Gly Gln Gln Thr Leu Lys Leu Arg Ile
                35                  40                  45
Thr Lys Gly Gly Pro Leu Pro Phe Ala Phe Asp Ile Leu Ser Ala Thr
50                  55                  60
Phe Thr Tyr Gly Asn Arg Cys Phe Thr Phe Tyr Pro Glu Asp Ile Ala
65                  70                  75                  80
Asp Tyr Phe Lys Gln Ser Phe Pro Glu Gly His Ser Trp Glu Arg Thr
                85                  90                  95
Met Met Tyr Glu Asp Gly Ala Cys Ser Thr Ala Ser Ala His Ile Ser
                100                 105                 110
Leu Lys Gly Thr Ser Phe Val His Asn Ser Thr Phe His Gly Val Asn
                115                 120                 125
Phe Pro Ala Asn Gly Pro Val Met Gln Lys Lys Thr Leu Asn Trp Glu
130                 135                 140
Pro Ser Ser Glu Lys Ile Thr Ala Cys Glu Gly Ala Leu Lys Gly Asp
145                 150                 155                 160
Val Thr Met Phe Leu Leu Leu Glu Gly Gly Leu Lys His Lys Cys Gln
                165                 170                 175
Phe Gln Thr Thr Tyr Glu Ala His Lys Ala Val Lys Met Pro Pro Ser
                180                 185                 190
His Ile Ile Glu His Arg Leu Val Arg Ser Glu Val Gly Ala Ala Val
                195                 200                 205
Gln Leu Arg Glu His Ala Val Ala Arg His Phe Ile Ala
                210                 215                 220
```

GREEN FLUORESCENT PROTEIN OPTIMIZED FOR EXPRESSION WITH SELF-CLEAVING POLYPEPTIDES

CONTINUING APPLICATION DATA

This application is the §371 U.S. National Stage of International Application No. PCT/US2007/026389, filed 28 Dec. 2007, which claims the benefit of U.S. Provisional Application Ser. No. 60/879,112, filed Jan. 5, 2007, each of which are incorporated by reference herein in their entireties.

BACKGROUND

Fluorescent proteins (FPs) constitute major research tools for the dissection of biological pathways at the cellular, subcellular, and molecular levels. The green fluorescent protein (GFP) from the jellyfish *Aequorea victoria* was the first fluorescent protein to be fully characterized and used. GFP rapidly became a major tool in molecular and cellular biology because it is naturally and spontaneously fluorescent and it can be fused to other proteins. This made GFP a biomarker of choice for a wide range of in vivo and in vitro applications. Following the initial discovery of *A. victoria* GFP, intensive research effort has resulted in the discovery, characterization and development of homologous fluorescent proteins with a wide range of optical and chemical properties. Fluorescent proteins from various species, including *Arthropoda, Hydrozoa*, and *Anthozoa* species, have now been characterized and several of their properties determine their usage. There is a present need to identify, modify, and optimize additional fluorescent proteins with characteristics that serve as novel and more efficient markers for in vivo and in vitro molecular imaging.

SUMMARY OF THE INVENTION

The present invention includes isolated polypeptides exhibiting fluorescence emission at a wavelength greater than about 500 nanometers (nm). In some embodiments, the isolated polypeptide absorbs at about 490 nm excitation wavelength. In some embodiments, the isolated polypeptide has a green fluorescent emission centered at about 508 nm. In some embodiments, the isolated polypeptides are efficiently released from polypeptidic constructs containing self-cleaving peptides. In some embodiments, the isolated polypeptide has an amino acid sequence with at least 80% sequence identity to SEQ ID NO:3. In some embodiments, the isolated polypeptide has an amino acid sequence with at least 90% sequence identity to SEQ ID NO:3. In some embodiments, the isolated polypeptide has an amino acid sequence with at least 95% sequence identity to SEQ ID NO:3. In some embodiments, the isolated polypeptide has the amino acid sequence SEQ ID NO:3.

Included in the present invention are isolated polypeptides encoded by a nucleotide sequence that hybridizes to SEQ ID NO: 1 or SEQ ID NO:2 under standard hybridization conditions. In some embodiments, the isolated polypeptide is encoded by SEQ ID NO:1 or SEQ ID NO:2. In some embodiments, the isolated polypeptides exhibit fluorescence emission at a wavelength greater than about 500 nm. In some embodiments, the isolated polypeptide absorbs at about 490 nm excitation wavelength. In some embodiments, the isolated polypeptide has a green fluorescent emission centered at about 508 nm. In some embodiments, such isolated polypeptides of the present invention are efficiently released from polypeptidic constructs containing self-cleaving peptides.

Included in the present invention are isolated nucleic acid sequences having at least 80% sequence identity to SEQ ID NO:1, the nucleic acid sequence encoding a polypeptide with a fluorescence emission at a wavelength greater than about 500 nm. In some embodiments, the isolated polypeptide absorbs at about 490 nm excitation wavelength. In some embodiments, the isolated polypeptide has a green fluorescent emission centered at about 508 nm. In some embodiments, the encoded polypeptide is efficiently released from polypeptidic constructs containing self-cleaving peptides. In some embodiments, the nucleic acid sequence includes SEQ ID NO:1 or SEQ ID NO:2.

The present invention includes such isolated nucleic acid sequences fused to a nucleic acid sequence encoding at least 5 amino acids other than the amino acids encoded by SEQ ID NO:1 or SEQ ID NO:2. In some embodiments, the isolated nucleic acid sequence is fused to a nucleic acid sequence encoding a self-cleaving peptide.

The present invention includes vectors including one or more isolated nucleic acid sequences of the present invention.

The present invention includes host cells including one or more of the isolated nucleic acid sequences of the present invention and/or one or more of the vectors of the present invention.

The present invention includes transgenic organisms or transgenic cells including one or more of the isolated fluorescent proteins of the present invention and/or one or more of the isolated nucleotide sequences of the present invention.

The present invention includes a virus including one or more of the isolated nucleic acid sequences of the present invention. The present invention includes cells including such a virus.

The present invention includes methods for identifying a cell wherein said method employs a vector of the present invention. In some embodiments of the method, the method employs microscopy. In some embodiments of the method, the method employs fluorescent activated cell sorting.

The terms "comprises" and variations thereof do not have a limiting meaning where these terms appear in the description and claims.

Unless otherwise specified, "a," "an," "the," and "at least one" are used interchangeably and mean one or more than one.

BRIEF DESCRIPTION OF THE DRAWINGS

FIGS. 1A and 1B present the cDNA nucleotide sequence and amino acid sequence of engineered *Corynactis viridis* fluorescent protein (FP). FIG. 1A provides the cDNA nucleotide sequence, without termination codon, (SEQ ID NO:2). FIG. 1B provides the amino acid sequence (SEQ ID NO:3).

FIG. 4 provides alignment (SEQ ID NO:6) of the amino acid sequences of native *C. viridis* GFP (SEQ ID NO:5) and engineered *C. viridis* FP (SEQ ID NO:3).

DETAILED DESCRIPTION AND ILLUSTRATIVE EMBODIMENTS OF THE PRESENT INVENTION

Figure 2:
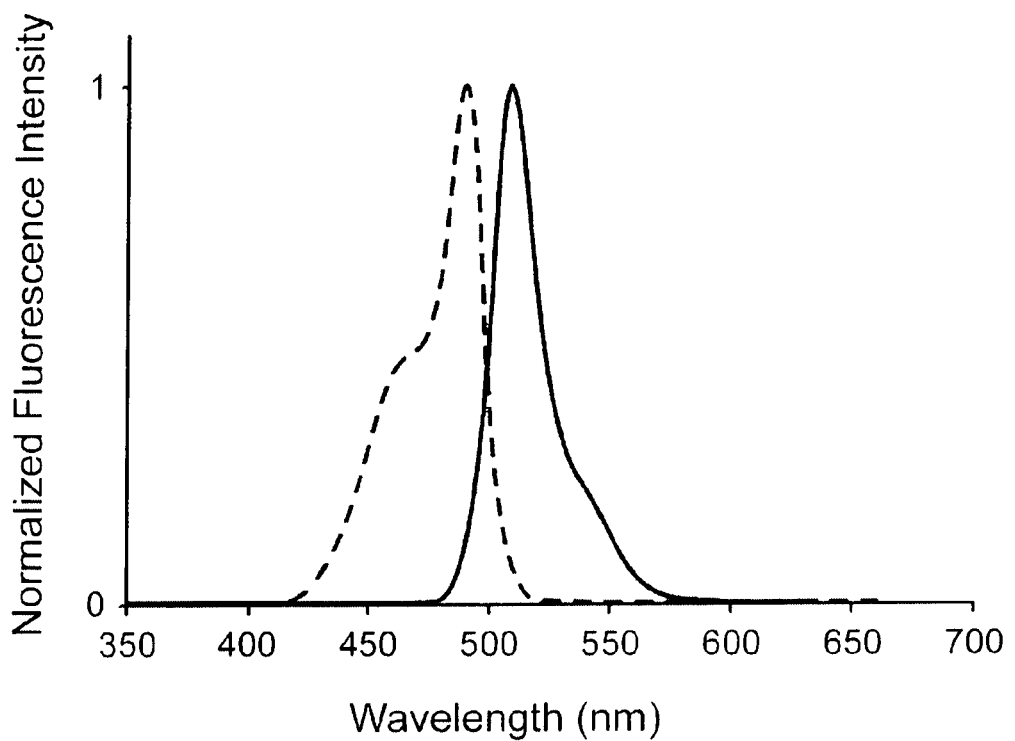
FIG. 2 indicates the absorption/emission spectra of the mature engineered *C. viridis* fluorescent protein. Normalized excitation fluorescence spectra is represented by a dashed line (- -) and emission fluorescence spectra is represented by the solid line (-).

The present invention provides a new fluorescent protein (FP). This protein has optical and physico-chemical properties that characterize it as a fluorescent protein. These properties make the subject protein useful for the various applications already established for other fluorescent proteins. In addition, the subject fluorescent protein has been specifically engineered to facilitate release from self-cleaving peptides. Therefore, it presents unique properties that make it an important addition to the range of fluorescent proteins known to date. For example, improved release from self-cleaving peptides allows the generation of novel types of expression vectors and reporter systems where a single promoter can drive the expression of the subject protein as a fluorescent marker together with other gene products that do not need to be tethered to the subject protein.

Useful FPs demonstrate one or more of the following properties. First, the FP should express efficiently, without toxicity and its fluorescence should be bright enough to provide sufficient signal above autofluorescence. Second, photostability of the FP should be compatible with its intended use. Third, if the FP is to be expressed as a fusion to another protein, it should remain fluorescent and it should not interfere with that protein's folding, cleavage and maturation processes. In addition, folding and maturation of the FP itself should not be impaired by its fused partner(s). Fourth, FP sensitivity to environmental changes should be compatible with their intended use. Characteristics that determine whether a particular FP meets these requirements include excitation and emission wavelength, number of spectral peaks, quantum efficiency, extinction coefficient, Stokes shift, degree of aggregation and oligomerization, time to maturation and ability to participate in fluorescence resonance energy transfer. The FPs of the present invention demonstrate one or more of these characteristics.

FP properties are typically determined by their structure and by the amino acid composition of their fluorophore. A number of domain and structural characteristics are shared among FPs from various species. Most FPs have a beta-can structure comprised of beta-sheets. The fluorophore is enclosed in the beta-can structure and it is often derived from a triplet of x-Y-G where x can vary significantly. The amino acid side chains protruding into the beta-can also affect optical properties of the FP.

The literature on FPs and chromoproteins is extensive. References cited herein are exemplary of this literature. In the patent literature, U.S Pat. No. 5,491,084 and U.S. Patent Applications 2002/0197676; 2003/0013849; 2003/0106078; 2005/0142637; and 2005/0196768 describe a number of FPs, their nucleic acid sequences, their characteristics and uses. The following scientific literature describes a number of FPs, their sequences, uses and characteristics as well as mutations and sequence modifications affecting their properties. Prasher et al., 1992, *Gene;* 111:229-33 (description of Green Fluorescent Protein from *Aequorea victoria*); Cubitt et al., 1995, *Trends Biochem. Sci.;* 20:448-55 (uses and limitations of GFP); Matz et al., 1999, *Nature Biotechnology;* 17:969-73 (description of Anthozoan GFP-like proteins); Fradkov et al., 2000, *FEBS Letters;* 479:127-30 (description of red-shifted Anthozoan FP); Gurskaya et al., 2002, *BMC Biochemistry;* 2:6 (modification of FPs by site-directed mutagenesis); Martynov et al., 2001, *J Biol Chem;* 276:21012-16 (description of the fluorophore from *Anemonia sulcata* FP); Yanushevich et al., 2002, *FEBS Letters* 511, 11-4 (introduction of mutations that reduce FP aggregation); Campbell et al., 2002, *PNAS;* 99:7877-82 (introduction of mutations to make a monomeric red FP); Bulina et al., 2002, *BMC Biochemistry;* 3:7 (introduction of mutations to change DsRed and as FP595 optical properties); Shaner et al., 2004, *Nature Biotechnology;* 22:1567-1572 (introductions of mutations and sequence modifications to generate improved monomeric red, orange and yellow FPs); Ando et al., 2002, *PNAS;* 99:12651-56 (description of an Anthozoan FP that converts from green to red fluorescence upon irradiation with UV light); Lippincott-Schwartz and Patterson, 2003, *Science;* 300:87-91 (use of FPs and contemporary imaging technologies to observe biological phenomena); Shagin et al., 2004, *Molecular Biology and Evolution;* 21:841-850 (review on the evolution of functional and structural features of metazoan GFP-like proteins); Shaner et al., 2005, *Nature Methods;* 2:905-909 (review on the properties and use of FPs); Erickson et al., 2003, *Biophysical Journal;* 85:599-611 (use of FRET between green and red fluorescent proteins); Szymczak et al., 2004, *Nature Biotechnology;* 22:589-594 (description of self-cleaving peptides). Additional information of FPs is available on the worldwide web, such as, for example, at clontech.com and evrogen.com.

With the present invention, a cDNA sequence (SEQ ID NO:4) encoding a fluorescent protein (FP) from *Corynactis viridis* (*Anthozoa, Corallimorpharia*) is provided. The native *C. viridis* FP (SEQ ID NO:5) has inherent optical and physico-chemical properties that characterize it as an FP. These properties make the *C. viridis* FP suitable for the various applications already established for other FPs. In addition, with the present invention, this protein has been genetically engineered to enhance specific properties. Specifically, the fluorescent protein of the present invention has been optimized for use in self-cleaving polypeptides, which is a major advantage of the present invention over previously described FPs. The fluorescent proteins of the present invention are readily synthesized in transgenic organisms using a wide range of expression constructs, including constructs expressing self-cleaving polypeptides.

A protein with optical and physico-chemical properties of green fluorescent proteins is provided. The subject protein is an engineered variant of a green fluorescent protein isolated from the "jewel" anemone *C. viridis*. Amino acid (SEQ ID NO:3) and nucleotide sequences (SEQ ID NO:1) of the engineered protein are set forth in FIGS. 1A and 1B. These sequences present high homology to FPs described previously, such as *Aequorea victoria* GFP and anthozoan FPs from *Corynactis californica*, *Anemonia sulcata* and *Ricordea florida* as well as other FPs and their mutagenized variants. The subject protein was generated by modifying native *C. viridis* GFP to obtain an FP with higher expression levels, higher stability and maturation speed, lower level of aggregation and highly efficient release from self-cleaving polypeptides.

In some embodiments, a fluorescent protein of the present invention has 223 amino acids. The conventionally used numbering of GFP will be used here to describe various domains and mutations of the subject protein. In the fluorescent protein of the present invention, the fluorophore domain may contain a typical lysine-glycine (YG) couplet at positions 69 and 70. In addition, the fluorophore may contain a threonine (T) at position 68.

The engineered fluorescent proteins of the present invention exhibit a fluorescence emission at a wavelength greater than about 500 nm. In some embodiments, a fluorescent protein of the present invention exhibits a green fluorescence emission at a wavelength of about 505 nm. In some embodiments, a fluorescent protein of the present invention exhibits a green fluorescence emission at a wavelength of about 488 nm to about 508 nm. In a preferred embodiment, a fluorescent protein of the present invention absorbs at about 490 nm excitation wavelength and has a green fluorescent emission centered at about 508 nm.

In some embodiments, a fluorescent protein of the present invention exhibits a cyan fluorescence emission at a wavelength of about 485 nm. In some embodiments, a fluorescent protein of the present invention exhibits a yellow fluorescence emission at a wavelength of about 540 nm. In some embodiments, a fluorescent protein of the present invention exhibits a red fluorescence emission at a wavelength of greater than about 580 nm, including, for example, a red fluorescence emission at a wavelength of about 583 nm or about 600 nm.

The engineered fluorescent proteins of the present invention exhibits rapid maturation, even at cool temperatures. The subject protein also exhibits high stability across a range of pH values and ionic strengths. The subject protein has a very low level of aggregation, generally not greater than monomeric and rarely greater than dimeric.

To develop the fluorescent protein of the present invention, site-directed PCR mutagenesis and random mutagenesis followed by DsRed FRET analysis as described by Erickson et al., 2003, *Biophysical Journal;* 85:599-611 and Szymczak et al., 2004, *Nature Biotechnology;* 22:589-594 revealed that the following mutations improve the release of *Corynactis viridis* GFP from self-cleaving peptides.

A preferred embodiment of the fluorescent protein of the present invention includes the following mutations: insertion of a Valine (V) residue at position 2; insertion of a Glycine (G) residue at position 7; substitution of a Serine (S) residue for an Asparagine (N) residue at position 28; substitution of a Threonine (T) residue for an Asparagine (N) residue at position 36; and substitution of a Lysine (K) residue for an Arginine (N) residue at position 219. In addition, silent nucleotide mutations were introduced throughout the gene to remove restriction sites and optimize codon usage for use of the subject FP in a wide range of organisms. The final result of this engineering process is presented as SEQ ID NO:1. The present invention also includes fluorescent proteins with one or any combination of more than one of the above described amino acid changes. Also included in the present invention are fluorescent proteins with one or any combination of more than one of these silent nucleotide mutations.

In the comparison of two amino acid sequences, structural similarity may be referred to by percent "identity" or may be referred to by percent "similarity." "Identity" refers to the presence of identical amino acids and "similarity" refers to the presence of not only identical amino acids but also the presence of conservative substitutions.

Fluorescent proteins of the present invention include polypeptides with at least about 80%, at least about 85%, at least about 90%, at least about 95%, at least about 96%, at least about 97%, at least about 98%, or at least about 99% amino acid sequence similarity to the amino acid sequence of SEQ ID NO:3. Fluorescent proteins of the present invention include polypeptides with at least about 80%, at least about 85%, at least about 90%, at least about 95%, at least about 96%, at least about 97%, at least about 98%, or at least about 99% amino acid sequence identity to the amino acid sequence of SEQ ID NO:3. In some embodiments, such polypeptides exhibit fluorescence emission at a wavelength greater than about 500 nm. In some embodiments, such polypeptides absorb at about 490 nm excitation wavelength and/or have a green fluorescent emission centered at about 508 nm. In some embodiments such polypeptides also exhibit a high efficiency of release from polypeptidic constructs containing self-cleaving peptides, and complements thereof.

Fluorescent proteins of the present invention include polypeptides with at least about 80%, at least about 85%, at least about 90%, at least about 95%, at least about 96%, at least about 97%, at least about 98%, or at least about 99% amino acid sequence similarity to the amino acid sequence of SEQ ID NO:5. Fluorescent proteins of the present invention include polypeptides with at least about 80%, at least about 85%, at least about 90%, at least about 95%, at least about 96%, at least about 97%, at least about 98%, or at least about 99% amino acid sequence identity to the amino acid sequence of SEQ ID NO:5. In some embodiments, such polypeptides exhibit fluorescence emission at a wavelength greater than about 500 nm. In some embodiments, such polypeptides absorb at about 490 nm excitation wavelength and/or have a green fluorescent emission centered at about 508 nm. In some embodiments such polypeptides also exhibit a high efficiency of release from polypeptidic constructs containing self-cleaving peptides, and complements thereof.

The present invention also includes fragments of the fluorescent proteins described herein. As used herein, a "fragment" means a polypeptide that has been truncated at the N-terminus, the C-terminus, or both. A fragment may range from about 5 to about 225 amino acids in length. For example it may be about 5, about 10, about 20, about 25, about 50, about 75, about 100, about 125, about 150, about 175, about 200, or about 225 amino acids in length. The present invention also includes polynucleotide encoding such polypeptide fragments.

The present invention also includes isolated polynucleotides that hybridize to SEQ ID NO:1, SEQ ID NO:2, and/or SEQ ID NO:4 under stringent hybridization conditions, wherein the polynucleotide encodes a polypeptide exhibiting fluorescence emission at a wavelength greater than about 500 nm. In some embodiments, such a polypeptide absorbs at about 490 nm excitation wavelength and/or has a green fluorescent emission centered at about 508 nm. In some embodiments such polynucleotide encodes a polypeptide that also exhibits a high efficiency of release from polypeptidic constructs containing self-cleaving peptides. The present invention also includes polypeptides encoded by such polynucleotides. For example, the FP of the present invention allows high-efficiency co-translational cleavage within viral 2A peptides fused its—and/or C-termini.

As used herein, "stringent hybridization conditions" refer to hybridization conditions such as 6×SSC, 5× Denhardt, 0.5% sodium dodecyl sulfate (SDS), and 100 µg/ml fragmented and denatured salmon sperm DNA hybridized overnight at 65° C. and washed in 2×SSC, 0.1% SDS at least one time at room temperature for about 10 minutes followed by at least one wash at 65° C. for about 15 minutes followed by at least one wash in 0.2×SSC, 0.1% SDS at room temperature for at least 3-5 minutes. Typically, a 20×SSC stock solution contains about 3M sodium chloride and about 0.3M sodium citrate.

Also included in the present invention are polynucleotides having a sequence identity of at least at least 80%, at least 85%, at least 90%, at least 95%, at least 96%, at least 97%, at least 98%, or at least 99% with the nucleotide sequence of SEQ ID NO:1, SEQ ID NO:3, or SEQ ID NO:4, where the polynucleotide encodes a polypeptide exhibiting fluorescence emission at a wavelength greater than about 500 nm. In some embodiments, such a polypeptide absorbs at about 490 nm excitation wavelength and/or has a green fluorescent emission centered at about 508 nm. In some embodiments such polynucleotide encodes a polypeptide that also exhibits a high efficiency of release from polypeptidic constructs containing self-cleaving peptides. As used herein, "sequence identity" refers to the identity between two polynucleotide sequences. Sequence identity is generally determined by aligning the residues of the two polynucleotides (for example, aligning the nucleotide sequence of the candidate sequence and the nucleotide sequence of SEQ ID NO:1 to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate sequence is the sequence being compared to a known sequence, such as SEQ ID NO:1. For example, two polynucleotide sequences can be compared using the Blastn program of the BLAST 2 search algorithm, as described by Tatiana et al., 1999, *FEMS Microbiol Lett.;* 174: 247-250, and available on the world wide web at ncbi.nlm.nih.gov/BLAST/. The default values for all BLAST 2 search parameters may be used, including reward for match=1, penalty for mismatch=−2, open gap penalty=5, extension gap penalty=2, gap x_dropoff=50, expect=10, wordsize=11, and filter on.

Also included in the present invention are polynucleotide fragments. A polynucleotide fragment is a portion of an isolated polynucleotide as described herein. Such a portion may be several hundred nucleotides in length, for example about 100, about 200, about 300, about 400, about 500, about 600, or about 700, nucleotides in length. Such a portion may be about 10 nucleotides to about 100 nucleotides in length, including but not limited to, about 14 to about 40 nucleotides in length.

Also included in the present invention are complements of the polynucleotides described herein. As used herein, "complement" and "complementary" refer to the ability of two single stranded polynucleotides to base pair with each other, where an adenine on one polynucleotide will base pair to a thymine on a second polynucleotide and a cytosine on one polynucleotide will base pair to a guanine on a second polynucleotide. Two polynucleotides are complementary to each other when a nucleotide sequence in a polynucleotide can base pair with a nucleotide sequence in a second polynucleotide. For instance, 5'-ATGC and 5'-GCAT are complementary. Typically two polynucleotides are complementary if they hybridize under the standard conditions referred to herein.

The fluorescent protein of the present invention offers many opportunities for various modifications, mutations and molecular engineering for future improvements. The composition of the subject protein is flexible enough so that replacing, deleting or inserting one or several amino acids may provide different physico-chemical properties and improved fluorescence characteristics. To alter the subject protein properties, modifications may be generated within or across the following conventionally used amino acid categories:
  aromatic amino acids: F, Y and W;
  positively charged amino acids: K, R and H;
  negatively charged amino acids: D and E;
  uncharged polar aliphatic amino acids: S, T, N, Q and M (C may be included in this category); and/or
  non-polar aliphatic amino acids: G, A, V, L and I (C and P may be included in this category).

For example, to reduce aggregation, it is possible to modify amino acids whose side groups extend outwardly from hydrophobic amino acids to hydrophilic amino acids including charged amino acids. Typically, the side chain may be moved outwardly or inwardly by replacing a hydrophobic non-polar amino acid with an uncharged polar amino acid or a charged polar amino acid. In addition, hydrophobic aromatic amino acids may be replaced with hydrophobic aliphatic amino acids and vice versa (see Vingron and Waterman, 1994, *J Mol Biol;* 233:1-12; Shaner et al., 2004, *Nature Biotechnology;* 221:1567-1572).

With the fluorescent proteins of the present invention, some of its fragments may be replaced or combined with fragments from other chromophoric proteins or FPs to obtain new proteins with different optical and physico-chemical properties. Fragments of interest from the subject protein include amino acids from about position 10 to about position 100, particularly fragments including the fluorophore. Part or all of the first approximately 45 amino acids of the subject FP may be replaced with a fragment from another protein to modify the subject protein's aggregating properties, ability to function as a fusion protein and ability to be released from a self-cleaving polypeptide. Amino acids from about position 93 on may be substituted with fragments from other proteins that will modify the subject protein's optical properties. Part or all of the last approximately 22 amino acids of the subject protein may be replaced with a fragment from another protein to modify the subject protein's ability to function as a fusion protein and its ability to be released from a self-cleaving polypeptide. Combining fragments from different proteins is readily accomplished by molecular engineering of the subject nucleotide sequence in a cloning or expression vector (see Vingron and Waterman, 1994, *J Mol Biol;* 233:1-12; Shaner et al., 2004, *Nature Biotechnology;* 22:1567-1572).

Aggregation level of the fluorescent proteins of the present invention may be further decreased by engineering a variant where two monomers are joined by a linker to promote internal dimerization. This type of modification typically prevents aggregation. Polypeptidic or chemical linkers may be used to join the C-terminal amino acid of one monomer to the N-terminal amino acid of another monomer of the subject protein. A number of amino acid groups can be used to link monomers including a polycysteine with an arsenic derivative, lysines and glutamates in the appropriate consensus sequence for transamination or a polyhistidine with a nickel derivative.

The fluorescent protein of the present invention has been engineered to retain useful properties when fused to a wide variety of other polypeptides. This type of fusion is of particular interest in the study of polypeptide properties and localization. Polypeptides fused to the subject FP or its fragments may be synthetic or from any natural source such as viruses, prokaryotes, eukaryotes, including protists, fungi, algae, plants, invertebrates and vertebrates. Polypeptides fused to the subject FP or its fragments may be receptors, signaling proteins, transcription factors, housekeeping proteins, adhesion proteins, structural proteins, regulatory proteins, enzymes, proteases, etc.

The design of the fluorescent protein of the present invention also allows for the addition of relatively short amino acid sequences to provide additional properties. For example, about 2 to about 200 or more amino acids may be added to provide an epitope, a fluorescent entity, a binding domain, a protease cleavage site, a self-cleaving peptide, etc.

The fluorescent protein of the present invention may be used in combination with other FPs. For example, it is possible to join the subject FP to another fluorescent entity to extend the Stokes shift. It is also possible to combine the subject FP with other FPs to induce fluorescence resonance energy transfer (FRET). FRET is used to perform various measurements in a wide range of experimental conditions.

To perform FRET-based measurements, the subject protein may be maintained within energy transfer distance of another fluorescer by a polypeptide of interest. The polypeptide may retain constant properties and only serve as a linker. The polypeptide may also have variable properties. For example, the linker may contain a consensus sequence for the cleavage site of a protease of interest. In the absence of the protease, FRET occurs and fluorescence is emitted by both fluorescers.

In the presence of active forms of the protease, the linker is cleaved, FRET is no longer possible and only one fluorescer emits fluorescence. Therefore, this kind of linker helps detect the protease activity.

To perform other types of FRET-based measurements, it is possible to use a linker that brings the subject protein and the other fluorescer within energy transfer distance only under certain conditions. For example, the linker may be composed of two components that complex under specific environmental conditions. For example, the two components of the linker may be a receptor and its one of ligands or an antibody and one of its epitopes. In this case each fluorescer may be joined to one of the linker components and FRET is detected only when environmental conditions enable the two linker components to form a complex. In another example, the linker may change conformation under certain conditions. In this case, fluorescers are brought within energy transfer distance and FRET is detected only when the linker adopts a specific conformation. These techniques find extensive applications including in indicators for calcium or cGMP measurements, Ras, Rap1 and Ran activity, kinase activity, etc.

To perform FRET-based measurements, the fluorescer used in combination with the subject FP may be another FP or any other fluorescer with the appropriate absorption or emission overlap such as biarsenical compounds.

It is also possible to use the linkers described above to combine the fluorescent protein of the present invention with a quencher instead of another fluorescer. In this case, fluorescence is only observed when the subject FP and the quencher are separated.

It is also possible to use fragments of the fluorescent protein of the present invention with the linkers described above for FRET. In this case, the subject FP is reconstituted and fluorescence is emitted only when the linker adopts a specific conformation.

The fluorescent protein of the present invention also allows for the introduction of silent or non-silent modifications of the nucleotide sequence. Typically, silent nucleotide sequence modifications may be performed to change the codon usage of the subject FP and make it match the codon usage of the host where it is expressed. Non-silent nucleotide sequence modifications may be performed to generate the amino acid sequence changes indicated above. Therefore, modifications in the nucleotide and amino acid sequences of the subject protein can involve changes in one or more nucleotides, one or more codons, or stretches of nucleotides as well as deletions from the natural sequence and replacements of portions of the natural sequence, or combinations thereof.

Various nucleic acid sequences encoding the subject protein, including DNA, RNA and modifications thereof retaining all or part of the coding sequence, can be used in a variety of ways. Nucleic acid sequences from the subject FP may be single or double stranded, sense (positive) or antisense (negative) sequences. These sequences may be modified in several ways including truncation, insertions and extensions. Fragments of about 12 to about 100 nucleotides may be used as primers to, for example, amplify all or part of the FP gene or fusion products containing the FP gene; isolate all or part of the subject FP gene; screen for the presence of all or part of the subject FP gene; identify FPs other than the subject FP but with substantial homology to the subject FP; modify the subject FP by site-specific mutagenesis; and synthesize modified forms of the subject FP. Fragments of about 10 to about 30 nucleic acids can be used, for example, in single stranded forms, double stranded forms, short hairpin RNAs, microRNAs or small interfering RNAs to alter the expression of the subject FP by RNA interference or other DICER-mediated mechanisms. Fragments of about 20 to about 1000 nucleotides can be used, fore example, in a variety of blot-based assays, including dot blots, northern blots, southern blots, and in in situ-hybidization assays to search for homologous FPs other than the subject FP or to detect the presence of all or part of the subject FP RNA or DNA in a variety of material, including DNA preparations, RNA preparations, cell samples, tissue samples or whole organisms.

The native *C. viridis* GFP gene could be directly isolated from a *C. viridis* specimen and GFP synthetized by engineering the native gene to obtain the subject amino acid and nucleotide sequences and associated protein properties. However, these costly and time-consuming procedures are no longer necessary since protein and nucleotide sequences of the subject FP are provided by the present invention. The gene or cDNA encoding the subject FP can now be maintained in DNA vectors and expression constructs for use in a variety of applications.

The FP polypeptides and nucleotide sequences of the present invention have a wide variety of applications, including, but not limited to any of those discussed herein. For example, a FP of the present invention may be used in conjugation with dendrimers and dendritic polymers. Such molecules are capable of translocation through the cell membrane for intracellular delivery of small molecule drugs, bioactive peptides, and proteins. See, for example, Chung et al., 2004, *Biopolymers;* 76(1):83-96.

An expression construct may be used where the gene or cDNA encoding the subject FP is inserted in a vector which enables the expression of the subject protein into a host organism. Typically, an expression construct includes transcriptional and translational regulatory regions that control expression of the subject FP in the host organism. Once expressed, the subject FP may be observed within the host organism for the investigation of cells, tissues, proteins, cellular pathways, phenotypes, genotypes, changes to environmental conditions, etc. If the subject protein is to be used in a purified form, it may be extracted from the host organism by conventional purification methods (see, for example, Sambrook, Fritsch and Maniatis "Molecular Cloning: A Laboratory Manual" Second Edition (1989) Cold Spring Harbor Laboratory Press, Cold Spring Harbor, N.Y.; Ausubel, Brent, Kingston, Moore, Seidman, Smith and Struhl. (2003) Current protocols in molecular biology. John Wiley & Sons, Inc., New York, N.Y.).

The fluorescent protein of the present invention may be used with a wide variety of DNA or RNA vectors, including plasmids, cosmids, phagemids, viral vectors, Yeast Artificial Chromosomes (YAC), Bacterial Artificial Chromosomes (BAC) or Human Artificial Chromosomes (HAC). In addition to the subject FP gene or cDNA, vectors used with the subject FP may contain restriction sites, multiple cloning sites, origins of replication for one or more hosts, selection markers (including constructs providing antibiotic resistance, change in color or change in metabolic abilities), PCR initiation sites. Vectors may also contain integration sequences, transposons and enzymes mediating DNA integration, constitutive or inducible promoters and other transcription regulatory sequences, transcription enhancers, translation regulatory sequences and sequences facilitating the isolation of the vector.

The fluorescent protein of the present invention may be used in multicistronic vectors or vectors expressing several proteins in the same transcriptional unit. Such vectors may use internal ribosomal entry sites (IRES). Since IRES are not functional in all hosts and do not allow for the stoichiometric expression of multiple protein, self-cleaving peptides may be used instead. For example, several viral peptides are cleaved during translation and allow for the expression of multiple proteins form a single transcriptional unit. Such peptides include 2A-peptides, or 2A-like sequences, from members of the Picornaviridae virus family. See for example Szymczak et al., 2004, *Nature Biotechnology;* 22:589-594. The subject FP has been engineered to be efficiently released from constructs containing self-cleaving peptides.

When expression of a fluorescent protein of the present invention is required, nucleotide sequences encoding the subject FP may be placed under the control of promoters, transcriptional and translational regulatory sequences that are functional in the chosen host. A large number of promoters have been identified in various hosts. These promoters may be of viral, animal or vegetal origins, they can originate from prokaryotes or eukaryotes or they can be entirely or partially synthetic.

Promoters used to regulate expression of the subject FP may be constitutive. For example, such promoters include but are not limited to human cytomegalovirus (CMV) promoters, SV40 promoters, elongation factor promoters (including xenopus and zebrafish EF-1alpha promoters), the cauliflower mosaic virus (CaMV) promoter, actin promoters, vertebrate and invertebrate tyrosine hydroxylase promoters and Prion protein promoters (see Udvadia and Linney, 2003, *Dev. Biol.;* 256:1-17; Friggi-Grelin et al., 2003, *J Neurobiol;* 54:618-627; Guilley et al, 1982, *Cell;* 30:763-773).

Promoters used to control expression of a fluorescent protein of the present invention may be inducible and allow for the expression of the subject FP only under specific environmental conditions. For example, such promoters include but are not limited to heat stress proteins (hsp) promoters, Gal-4/UAS promoter systems or Tet-regulated promoters (see Urlinger et al., 2000, *PNAS;* 97:7963-7968; Ristevski, 2005, *Mol Biotechnol.;* 29:153-163; Duffy, 2002, *Genesis;* 34:1-15; Udvadia and Linney, 2003, *Dev. Biol.;* 256:1-17.

A fluorescent protein of the present invention may be used in gene trap vectors. In this case, the vector does not contain a promoter for expression of the subject FP. Instead, a splice-accepting sequence is placed upstream of the subject FP gene or cDNA and the vector is introduced in a suitable host for random integration into the host's genomic DNA. Expression of the subject FP is then observed if integration places the subject FP gene under the control of one of the host's promoter sequences. This technique is typically used for insertional mutagenesis, genetic screens or to isolate cell- or tissue-specific promoters (see Leighton et al., 2001, *Nature;* 410:174-179; Gong et al., 2001, *Genetica;* 111:213-225; Kawakami, 2005, *Dev Dyn;* 234:244-254).

Vectors containing a gene or cDNA encoding a fluorescent protein of the present invention may be introduced into a wide variety of unicellular or multicellular, prokaryotic or eukaryotic, hosts such as protists, fungi, algae, plants, invertebrates and vertebrates. Suitable hosts include but are not limited to hosts employed in the scientific literature such as mammalian cell lines including stem cells, zebrafish *Danio rerio*, the nematode *Caenorhabditis elegans*, the fruit fly *Drosophila melanogaster*, the bacteria *Escherischia coli*, yeast species, the plant *Arabidopsis thaliana*, etc. Vectors containing the subject FP gene or cDNA may integrate into the host genome or remain extrachromosomal.

Vectors containing the subject FP gene or cDNA may be introduced into progenitor cells for random integration or homologous recombination into the host genome and the generation of transgenic lines of organisms.

Vectors containing the subject FP gene or cDNA may be introduced into the chosen host by any efficient and convenient technique, including but not limited to, transfection, electroporation, lipofection, fusion, transformation, etc. Hosts where introduction of the vector has been successful may be selected by using selection markers provided by the vector or by observing fluorescence emitted by the subject FP.

It is evident that the subject FP can be used to replace FPs described previously or in combination with such FPs. The subject FP may be used with a number of measurement and detection devices including but not limited to epifluorescence microscopes, confocal microscopes, two-photons microscopes, fluorescence activated cell sorters (FACS), fluorescent speckle spectroscopy, etc.

The fluorescent protein of the present invention contains epitopes that may be used for the preparation of antibodies in accordance with established techniques. See for example Zola (2000), Monoclonal Antibodies: Preparation and Use of Monoclonal Antibodies and Engineered Antibody Basics, Bios Scientific Publisher Ltd, Springer-Verlag, N.Y. and Lidell and Cryer (1991) A Practical Guide to Monoclonal Antibodies, John Wiley & Sons. The present invention includes such antibodies. Antibodies that bind to epitopes of the subject FP may be used in a variety of applications including, but not limited to, purification of fluorescent proteins of the present invention or fusion constructs thereof and for cyto- and histochemical detection of the subject FP.

The present invention is illustrated by the following examples. It is to be understood that the particular examples, materials, amounts, and procedures are to be interpreted broadly in accordance with the scope and spirit of the invention as set forth herein.

EXAMPLES

*Corynactis viridis* specimens were collected off the French Atlantic coast (Arcachon Bay, France). Whole animals were frozen for total RNA extraction. Total RNA was extracted using RNAble buffer (Eurobio). Messenger RNAs were purified from total RNAs using mRNA Purification Kit cat. #27-9258-01 from GE Healthcare. First strand cDNA was synthetized using the ImProm-II Reverse Transcription System (Promega).

*C. viridis* fluorescent protein (FP) cDNA was amplified from first strand cDNA by Polymerase Chain Reaction (PCR) with a set of degenerate primers (Eurogentec) on a Perkin Elmer GenAmp PCR System 2400. Amplifications were carried out in 25 microliter (μl) reaction mixtures containing 10-50 nanograms (ng) cDNA target, 50-100 ng of each degenerate primer, 200 micromolar (μM) deoxyribonucleoside 5-triphosphates (dNTPs), 2.5 millimolar (mM) MgCl2, and 1 unit of PfuTurbo DNA Polymerase (Stratagene catalog #600250). PCR products with the expected size were cloned with a TOPO-TA Cloning kit (Invitrogen). Cloned cDNA fragments were then subcloned in the pQE-TriSystem vector (Qiagen) transformed in electrochemically competent *E. coli* and plated on LB plates supplemented with ampicillin and IPTG to induce FP expression.

After overnight culture at 37° C., *E. coli* colonies were screened for fluorescence using a stereomicroscope (Leica MZ FL III). Fluorescent colonies were replated as streaks onto new LB plates supplemented with ampicillin and IPTG, grown overnight at 37° C. and screened for fluorescence a second time to confirm fluorescence emission. Fluorescent bacterial clones were then grown overnight at 37° C. in liquid LB cultures supplemented with ampicillin for plasmid isolation and sequencing.

The native cDNA sequence of *C. viridis* FP is:

(SEQ ID NO: 4)
ATGAGCCTGAGCAAGCACGTGATCGCCCAGGACGTGACCATGATC

TACCGCATGGACGGCTGCGTGAACGGCCACAGCTTCACCATCGAG

GGCGAGGGTACCGGCAAGCCCTACGAGGGCCAGCAAACCCTGAAG

CTCCGCATCACCAAGGGCGGCCCCCTGCCCTTCGCCTTCGACATC

TTGAGCGCCACCTTCACCTACGGCAACCGCTGCTTCACCTTCTAC

CCCGAGGACATCGCCGACTACTTCAAGCAGAGCTTCCCCGAGGGC

CACATGGGAACGCACCATGATGTACGAGGACGGCGCCTGCTCCAC

CCCAGCGCCCACATCAGCCTGAAGGGCACCAGCTTCGTGCACAAC

AGCACCTTCCACGGGGTGAACTTCCCCGCCAACGGCCCCGTGATG

CAGAAGAAGACCCTGAACTGGGAGCCCAGCTCCGAGAAGATCACC

GCCTGCGAGGGCGCCCTGAAGGGGGACGTGACCATGTTCCTCCTC

CTGGAGGGCGGCCTGAAGCACAAGTGCCAGTTCCAGACCACCTAC

GAGGCCCACAAGGCCGTGAAGATGCCCCCCTCCCACATCATCGAG

CACCGCCTGGTGCGCAGCGAGGTGGGCGCGGCCGTGCAGCTGCGC

GAGCACGCCGTGGCCAAGCACTTCATCGCCTAA.

The native amino acid sequence *C. viridis* FP is:

(SEQ ID NO: 5)
MSLSKHVIAQDVTMIYRMDGCVNGHSFTIEGEGTGKPYEGQQTLKLR

ITKGGPLPFAFDILSATFTYGNRCFTFYPEDIADYFKQSFPEGHSWE

RTMMYEDGACSTASAHISLKGTSFVHNSTFHGVNFPANGPVMQKKTL

NWEPSSEKITACEGALKGDVTMFLLLEGGLKHKCQFQTTYEAHKAVK

MPPSHIIEHRLVRSEVGAAVQLREHAVAKHFIA.

To obtain the FP of the present invention, engineering of the native *C. viridis* FP sequences was performed by site-directed PCR mutagenesis using the GeneTailor system (Invitrogen) and random mutagenesis using the Diversify PCR Random Mutagenesis Kit (Clontech). To obtain FP exhibiting optimal release from self-cleaving peptides, Corynactis FPs were linked to DsRed (Clontech) by a T2A peptide and cleavage efficiency was determined using DsRed FRET analysis as described by Erickson et al., 2003, *Biophysical J;* 85:599-611 and Szymczak et al., 2004, *Nature Biotechnology;* 22:589-594. DsRed was used as a FRET partner for the engineered FP because it forms oligomers, and thus provided very stringent conditions for the evaluation of release efficiency. Stringent conditions allowed the engineering of an FP that can be efficiently released from self-cleaving peptides fused to complex proteins. This ensured that the engineered FP could be used in a wide range of experimental conditions. Several cycles of site-directed PCR mutagenesis and random mutagenesis were performed to obtain a FP which allows for optimal release from self-cleaving polypeptides and optimal fluorescence emission in fusion protein constructs. To determine the protein's optical and physico-chemical properties, the engineered FP was purified according to instructions provided by the pQE-TriSystem vector manufacturer (Qiagen).

For sequence analysis, five replicates of automated sequencing were used to verify the DNA sequence of the engineered fluorescent protein. Parent sequences are presented below.

The engineered *C. viridis* FP, including a termination codon, is encoded by the DNA sequence:

(SEQ ID NO: 1)
ATGGTGAGCCTGAGCAAGGGCCACGTGATCGCCCAGGACGTGACCA

TGATCTACCGCATGGACGGCTGCGTGAACGGCCACAACTTCACCAT

CGAGGGCGAGGGTAACGGCAAGCCCTACGAGGGCCAGCAAACCCTG

AAGCTCCGCATCACCAAGGGCGGCCCCCTGCCCTTCGCCTTCGACA

TCTTGAGCGCCACCTTCACCTACGGCAACCGCTGCTTCACCTTCTA

CCCCGAGGACATCGCCGACTACTTCAAGCAGAGCTTCCCCGAGGGC

CACAGCTGGGAACGCACCATGATGTACGAGGACGGCGCCTGCTCCA

CCGCCAGCGCCCACATCAGCCTGAAGGGCACCTCCTTCGTCCATAA

TAGCACTTTCCACGGCGTCAACTTCCCCGCCAATGGCCCCGTCATG

CAGAAAAAGACTCTCAATTGGGAACCCAGCTCCGAGAAGATCACCG

CCTGCGAGGGCGCCCTGAAGGGGGACGTGACCATGTTCCTCCTCCT

GGAGGGCGGCCTGAAGCACAAGTGCCAGTTCCAGACCACCTACGAG

GCCCACAAGGCCGTGAAGATGCCCCCCTCCCACATCATCGAGCACC

GCCTGGTGCGCAGCGAGGTGGGCGCAGCCGTGCAGCTGCGCGAGCA

CGCCGTGGCCCGCCACTTCATCGCCTAA.

The engineered *C. viridis* FP has the following amino acid sequence:

(SEQ ID NO: 3)
MVSLSKGHVIAQDVTMIYRMDGCVNGHNFTIEGEGNGKPYEGQQTLK

LRITKGGPLPFAFDILSATFTYGNRCFTFYPEDIADYFKQSFPEGHS

WERTMMYEDGACSTASAHISLKGTSFVHNSTFHGVNFPANGPVMQKK

TLNWEPSSEKITACEGALKGDVTMFLLLEGGLKHKCQFQTTYEAHKA

VKMPPSHIIEHRLVRSEVGAAVQLREHAVARHFIA.

Nucleotide sequence homology to other known FPs was calculated by scoring the percentage of identical nucleotides in aligned sequences. Positions where alignment gaps occurred were ignored. Analysis revealed that no isolated nucleotide fragment of 30 nucleotides or more of SEQ ID NO:2 had more than 88% identity to any known FP sequence.

The alignment of the amino acid sequence of native *C. viridis* FP (SEQ ID NO:5) with the amino acid sequence of the engineered *C. viridis* (SEQ ID NO:3) along with a consensus sequence (SEQ ID NO:6) is shown in FIG. 4.

Amino acid sequence analysis revealed that the engineered protein exhibits less than 79% similarity to the next most closely related FP (ccal Orange Fluorescent Protein, GenBank Accession Number AAZ14789) and to the next most closely related patented FP (ccal YFP).

Absorption and emission spectra of the engineered FP are indicated in FIG. 2. Spectral characteristics of the engineered FP are indicated below in Table 1.

TABLE 1

Spectral characteristics of the mature protein.

| Excitation/Emission Maxima nm | Molar Extinction Coefficient $M^{-1} \cdot cm^{-1}$ | Fluorescence Quantum Yield | pH sensitivity | Number of Amino acids |
|---|---|---|---|---|
| 490/508 | 51,400 (490 nm) | 0.62 | pKa = 5.9 | 223 |

Figure 3:
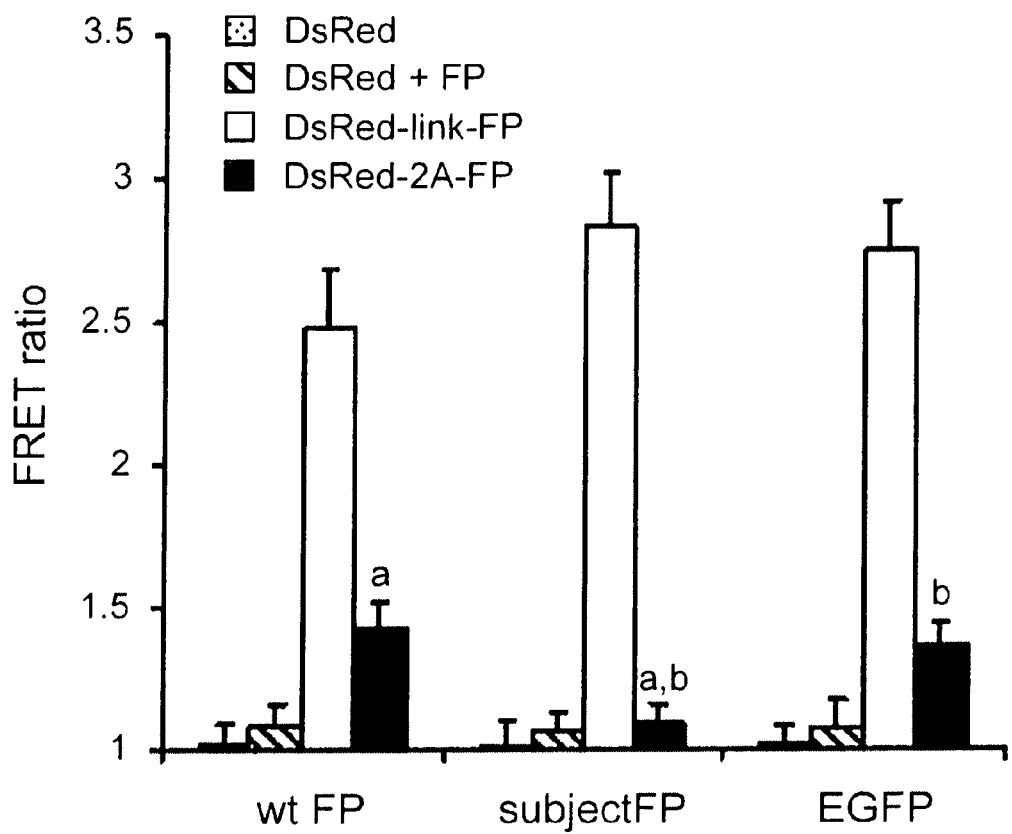
FIG. 3 presents release efficiency from self-cleaving peptides determined using FRET analysis.

Efficiency of release of the engineered FP from self-cleaving peptides was determined using FRET analysis in HEK293 cells as described by Erickson et al., 2003, *Biophysical Journal;* 85:599-611 and are shown in FIG. 3. Data are presented in FIG. 3 as means±SEM of FRET ratios where DsRed is used as an acceptor. Negative controls included expression of DsRed alone or co-expression of free forms of DsRed and green fluorescent proteins such as the wild-type form of *C. viridis* FP (wtFP), the engineered form of *C. viridis* or the widely used EGFP (Clontech). Data show that strong FRET is detected when the subject FP is tethered to DsRed by a non-cleavable linker (DsRed-link-FP). However FRET is reduced to levels which are non-significantly different from negative controls when the engineered FP is linked to DsRed by a self-cleaving peptide (DsRed-2A-FP). Data also show that when a self-cleaving peptide is used, FRET is significantly lower with the engineered FP than with the non-engineered form of the *C. viridis* FP (a, P<0.01). Therefore, the engineered FP is released more efficiently from multicistronic constructs that use self-cleaving peptides than the non-engineered form of the *C. viridis* FP or the commonly used EGFP. For example, a FRET ration of less than 1.5, less than about 1.25, or less than about 1.1 may be observed.

The engineered FP is well suited for expression in a wide range of organisms. It emits green fluorescence when expressed in bacteria (*Escherichia coli*), plant systems (*Arabidopsis thaliana*), invertebrates (*Caenorhabditis elegans*), fish (*Danio rerio*) and mammalian systems (Hela, HEK293 and PC12 cells).

The engineered FP of the present invention presents unique properties suitable for applications in particular contexts. Therefore, it is an important addition to the range of FPs known to date. Because it has been specifically engineered to facilitate release from self-cleaving peptides, the FP allows the generation of novel types of expression vectors and reporter systems where a single promoter can drive the expression of the engineered FP as a fluorescent marker together with other gene products that do not need to be tethered to the engineered FP. Since the engineered FP retains optimal properties when fused to other proteins, it also provides an alternative to the use of known FPs to investigate a wide range of molecular and cellular mechanisms, including but not limited to promoter activity, protein properties and protein localization. Since the engineered FP retains optimal properties in a wide range of hosts, it can be used in most applications of molecular biology.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims. All headings are for the convenience of the reader and should not be used to limit the meaning of the text that follows the heading, unless so specified. For any method disclosed herein that includes discrete steps, the steps may be conducted in any feasible order. And, as appropriate, any combination of two or more steps may be conducted simultaneously. Unless otherwise specified, "a," "an," "the," and "at least one" are used interchangeably and mean one or more than one.

SEQUENCE LISTING FREE TEXT

SEQ ID NO:1 Nucleotide sequence of engineered *C. viridis* FP, with termination codon.
SEQ ID NO:2 Nucleotide sequence of engineered *C. viridis* FP.
SEQ ID NO:3 Amino acid sequence of engineered *C. viridis* FP.
SEQ ID NO:4 Nucleotide sequence of native *C. viridis* FP.
SEQ ID NO:5 Amino acid sequence of native *C. viridis* FP.
SEQ ID NO:6 Consensus amino acid sequence.

What is claimed is:

1. An isolated polypeptide having an amino acid sequence with at least 95% sequence identity to SEQ ID NO:3, wherein the polypeptide exhibits fluorescence emission at a wavelength of about 508 nanometers (nm) and is released from polypeptidic constructs containing self-cleaving peptides, wherein the polypeptide comprises a fluorophore domain comprising a threonine at position 68, a tyrosine at position 69, and a glycine at position 70, and wherein the polypeptide further comprises a valine at position 2, a glycine at position 7, an asparagine at position 28, an asparagine at position 36, and an arginine at position 219.

2. The polypeptide of claim 1 having SEQ ID NO:3.

3. The polypeptide according to claim 1, wherein said polypeptide is encoded by SEQ ID NO: 1 or SEQ ID NO:2.

4. An isolated nucleic acid sequence having at least 95% sequence identity to SEQ ID NO:1, the nucleic acid sequence encoding a polypeptide with a fluorescence emission at a wavelength of about 508 nm and being released from polypeptidic constructs containing self-cleaving peptides, wherein the polypeptide comprises a fluorophore domain comprising a threonine at osition 68, a tyrosine at position 69, and a glycine at position 70 and further comprises a valine at position 2, a glycine at position 7, an asparagine at position 28, an asparagine at position 36, and an arginine at position 219.

5. An isolated nucleic acid sequence, wherein the nucleic acid sequence encodes a polypeptide of claim 1.

6. The nucleic acid sequence according to claim 4 comprising SEQ ID NO:1 or SEQ ID NO:2.

7. An isolated nucleic acid sequence according to claim 4 fused to a nucleic acid sequence encoding at least 5 amino acids other than the amino acids encoded by SEQ ID NO:1.

8. An isolated nucleic acid sequence according to claim 4 fused to a nucleic acid sequence encoding a self-cleaving peptide.

9. A vector comprising a nucleic acid sequence of claim 4.

10. An isolated host cell comprising a nucleic acid sequence of claim 4.

11. A nonhuman transgenic organism or an isolated transgenic cell comprising a fluorescent protein encoded by a nucleotide sequence of claim 4.

12. A virus comprising a nucleic acid sequence of claim 4.

13. An isolated cell comprising the virus of claim 12.

14. A method for detecting gene expression in a cell the method comprising detecting fluorescence emission at a wavelength of about 508 nanometers (nm) in a cell comprising a vector according to claim 9.

15. A method according to claim 14 wherein said method employs microscopy.

16. A method according to claim 14 wherein said method employs fluorescent activated cell sorting.

17. An isolated nucleic acid sequence encoding a polypeptide having an amino acid sequence with at least 95% sequence identity to SEQ ID NO:5, wherein the polypeptide exhibits fluorescence emission at a wavelength of about 508 nanometers (nm) and wherein the polypeptide comprises a fluorophore domain comprising a threonine at position 68, a tyrosine at position 69, and a glycine at position 70.

18. The polypeptide encoded by the isolated nucleic acid of claim 17.

19. An isolated nucleic acid sequence according to claim 5 fused to a nucleic acid sequence encoding at least 5 additional amino acids.

20. An isolated nucleic acid sequence according to claim 5 fused to a nucleic acid sequence encoding a self-cleaving peptide.

* * * * *